June 4, 1935. R. WITTERSTAETTER Plant Pat. 127

CARNATION VARIETY

Filed March 26, 1934

Richard Witterstaetter, deceased, Inventor,
by Richard C. Witterstaetter, Executor, By Murray and Zugelter
Attorneys.

Patented June 4, 1935

Plant Pat. 127

UNITED STATES PATENT OFFICE

127

CARNATION VARIETY

Richard Witterstaetter, deceased, late of Cincinnati, Ohio, by Richard C. Witterstaetter, executor, Cincinnati, Ohio, assignor to R. Witterstaetter Carnation Company, a partnership composed of Edward C. Deller, William H. Deller, and Edward A. Witterstaetter, Cincinnati, Ohio Application March 26, 1934, Serial No. 717,364

1 Claim. (Cl. 47—60)

Figures 1, 2, 3:
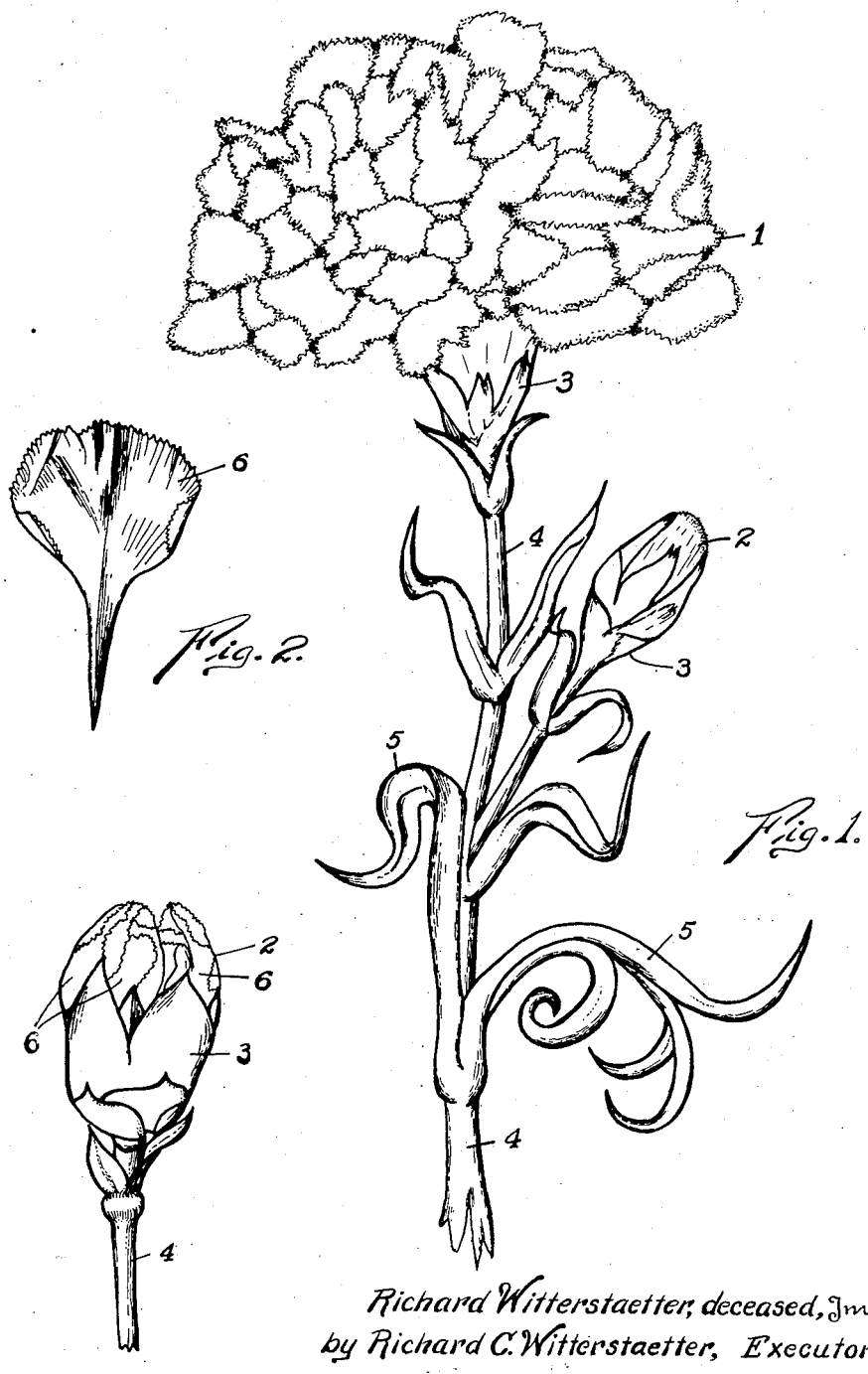

This invention relates to improvements in a carnation variety.

The invention has as its objects, the production of plants of the above character, in which: the bloom is characterized by its large size and fullness, its distinctive shade of pink, its early steady blooming and good keeping qualities, its perfect form and high build, and its very pronounced clove fragrance.

Other objects of the invention are to produce a plant of the above mentioned character, which grows strongly and rapidly, with substantial foliage and a rigid sturdy stem carrying a short but heavy and broad calyx that holds the large bloom unusually well without the premature splitting that commonly occurs in other varieties of large carnations. The plant blooms throughout the season.

In the drawing, Fig. 1 is a perspective view of the present plant showing the bloom, foliage and a bud; Fig. 2 is a representation of a petal and Fig. 3 shows a bud in detail.

The drawing figures disclose that much of the new plant as is necessary to illustrate the distinctive visible features thereof. The character 1 indicates the bloom or flower substantially fully developed, and 2 indicates a bud. The fully opened flower has 85 to 100 petals. Attention is directed to the perfect form of the bloom and the fullness of petals 6. The calyx 3 differs from that of ordinary large carnations, in that it is short and of comparatively large diameter. The calyx as well as the foliage is somewhat heavier than usual, which accounts for the non-splitting characteristic thereof and its ability to hold the bloom unusually well. The stem 4 is seen to be sturdy and slightly larger than the stems of other species, and it is further characterized by a pronounced rigidity. Except for a slight evidence of increased size and weight, the linear channeled leaves 5 follow very closely the form and color of leaves characteristic of large carnations heretofore known. The plant is found to produce more blooms than any other variety of large carnation.

The fragrance of the bloom is extraordinary and distinctive for its strong but sweet clove character. The increased fragrance is readily noticeable by comparison with that of the known varieties of carnations.

The improved plant of this invention was produced in the following manner, in the vicinity of Cincinnati, Ohio, with the employment of the same care and conditions normally given to the growing of carnations. A mother plant was produced by crossing the well-known Ward and Matchless carnations. The Ward is a medium pink carnation possessing good keeping qualities, and the Matchless is white with good keeping and blooming qualities, but rather poor form. The well-known light pink carnation Early Rose, whose blooming and keeping qualities are poor and whose stem is not rigid, was then crossed on the said mother plant to produce the carnation which is the subject of this invention. By the method above described, the rigid and stout stem of the mother plant was provided with a fragrant, full, and clear light pink flower unlike the flowers of any of the plants used in the production of the herein described new carnation. The characteristics of the plant, with reference to the Ridgway Color Chart, will now be set forth.

The inside of the petal is La France pink of Ridgway Color Chart, plate 1, 3, f. Outside of petal is paler than Pale Vinaceous pink, Ridgway plate XXVII, I'' f. General effect of the flower is La France pink the same as the inner surface of the petals. Sepals are usually five in number and occassionally six, and are heavy, strongly united, 1 inch long and broad, the apices thereof being broad and obtuse, terminating acutely. Sepals are of the color Pale Tiber green at base, Ridgway plate XVIII, 33', f., and Tiber green at broadest part, Ridgway plate XVIII 33' d. The foliage is heavy, the upper leaves being 3 to 4 inches long and up to $\frac{5}{16}$ inches wide, of color Dark bluish glaucous, Ridgway plate XLII, 37''' b. The leaves clasp the stems at the nodes. The stems are strong, and of substantially the color of the leaves before the bloom is rubbed off; after it is rubbed off, the color is Stone green, Ridgway plate XLII, 37'''. The scales extend up the calyx in pairs ⅝, ½ and ⅜ inch, while the width of the same scales at their widest part is ⅞, ½, and ⅜ inches respectively.

The bloom contains approximately three times as many petals as the ordinary carnation, making a bloom approximately four and one-half inches in diameter. In spite of the large size and fullness of the bloom, the short and broad calyx is found to hold the bloom well without splitting.

The type of calyx resulting is not clearly accounted for, as the calyces of the mother plant and Early Rose are not abnormal as to size, shape, or weight.

In the inventor's file, the mother plant is identified as #2104 K.

What is claimed is:

The herein-disclosed carnation variety, characterized by a large, full, highly built flower, of good keeping properties, and of an unusually pronounced clove fragrance, the plant being characterized further by its rigid stem and short, broad, heavy calyx which holds the large flower throughout the carnation season without premature splitting, substantially as shown and described.

RICHARD C. WITTERSTAETTER.

*Executor of the Last Will and Testament of Richard Witterstaetter, Deceased.*